United States Patent [19]

Hickey et al.

[11] Patent Number: 4,553,959

[45] Date of Patent: Nov. 19, 1985

[54] URETHRAL CATHETER

[75] Inventors: David S. Hickey, Fallowfield; John C. Brocklehurst, Wilmslow, both of England

[73] Assignee: The Victoria University of Manchester, Manchester, England

[21] Appl. No.: 460,041

[22] Filed: Jan. 21, 1983

[30] Foreign Application Priority Data

Jan. 27, 1982 [GB] United Kingdom ................ 8202371

[51] Int. Cl.[4] .............................................. A61M 25/00
[52] U.S. Cl. ..................................... 604/96; 604/105; 604/247; 604/282; 128/DIG. 25
[58] Field of Search ................. 604/96, 101, 105, 247, 604/256, 280–282; 128/DIG. 25

[56] References Cited

U.S. PATENT DOCUMENTS

| 504,424 | 9/1893 | De Pezzer | 604/104 |
|---|---|---|---|
| 1,596,754 | 8/1926 | Moschelle | 604/282 |
| 2,687,131 | 8/1954 | Raiche | 604/101 |
| 3,428,046 | 2/1969 | Remer et al. | 604/96 X |
| 3,598,126 | 8/1971 | Hoeltzenbein | 604/282 |
| 3,672,372 | 6/1972 | Heimlich | 604/247 X |
| 3,797,478 | 3/1974 | Walsh et al. | 128/DIG. 25 |
| 4,103,689 | 8/1978 | Leighton | 604/247 X |

Primary Examiner—Dalton L. Truluck
Attorney, Agent, or Firm—LeBlanc, Nolan, Shur & Nies

[57] ABSTRACT

A urethral catheter comprising a tube for insertion into the bladder and having an inlet (17) for the drainage of urine via the tube, and a wall portion (18) having reduced thickness and increased flexural properties such that this wall portion (18) will undergo substantially complete collapse under normal urethral pressure thus to comply with the irregular and slit-like lumen (11) but permit adequate distension for normal drainage.

11 Claims, 8 Drawing Figures

URETHRAL CATHETER

This invention concerns catheters of the kind used for drainage of the bladder via the urethra. All known forms of urethral catheter consist of a rigid or semi-rigid tube which is inserted into the bladder to effect rapid or controlled drainage thereof, the tube having an inlet and an outlet at the proximal and distal ends respectively. Such catheters serve as constant drainage devices wherein the tube remains open and is designed to resist any appreciable degree of collapse or compliance with the shape of the urethra.

Research conducted at the Victoria University of Manchester, has confirmed that the lumen of the male and female urethra is non-circular and tends towards a narrow slit. The slit-like shape is maintained even during micturition.

Existing catheters of rigid or semi-rigid circular cross-section cannot assume a close and compliant fit within the urethra, and this can result in leakage of urine on two sides of the catheter tube between the outer tube surface and the inner wall surface of the lumen. Such leakage produces wetness leading to discomfort, and increases the risk of infection leading to further discomfort and pain. Furthermore, the rigidity of existing catheters can cause abnormal urethral distension and damage which can produce further patient discomfort.

An object of the present invention is to provide a urethral catheter in which the aforementioned disadvantages are overcome and which will more approximately resemble the natural properties of the urethra.

According to the present invention there is provided a urethral catheter comprising a tube open at the proximal and distal ends respectively, the tube wall, throughout at least a portion of that part of the tube to be situated within the urethra, being sufficiently flexural that the maximum transmural pressure required to collapse the tube to half of its normal cross-sectional area is 100 centimeters water gauge.

Several embodiments of the invention will be described in further detail, by way of example only, with reference to the accompanying drawings, in which.

Figure 7:
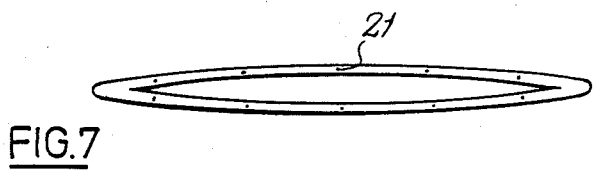

and FIG. 7 is a transverse section through a catheter wall being preformed for a purpose to be described.

Figure 1A:
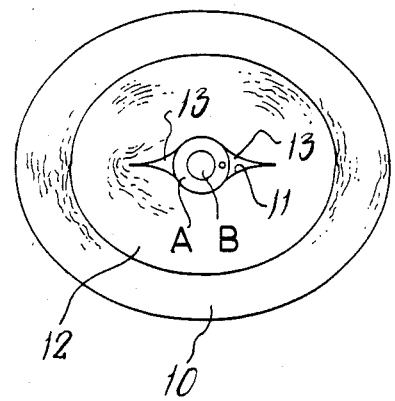
FIGS. 1a and 1b illustrate schematically, in transverse section, a urethral passage with, respectively, a known type of catheter, and one produced in accordance with the invention, in-situ.

Referring now to the drawings, FIG. 1a shows in transverse section the muscular wall 10 surrounding the urethral area, the lumen 11 being the actual passage communicating with the bladder, and the area known as the intima 12 which is situated between the muscular wall and the lumen. As can be seen from FIG. 1a when a rigid or semi-rigid catheter A is inserted in the lumen 11, the urethra is distended to leave free passages 13 on both sides of the catheter which are large enough to permit the bypass of urine. In the conventional catheter of the type illustrated at A, the tube is designed as a constant drainage device providing a continuous open passage B leading from the bladder, through which urine can drain continuously or intermittently without restriction.

Figure 1B:
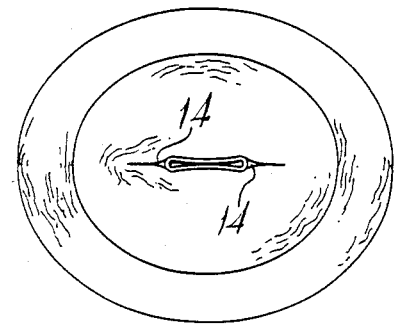

There is evidence, as discussed above that a catheter which can assume a non-circular form in situ could have considerable benefits to the patient. In particular, the female urethral lumen is proximally a horizontal slit which changes through a cruciate to a vertical slit at the external meatus. Furthermore, there is considerable variation between individuals both in shape and dimension. Therefore, by making the catheter walls very thin and flexible the tube can mould itself more closely to the shape of the closed urethral walls. Such an arrangement is illustrated in-situ in FIG. 1b where the compliance of the catheter wall is such that the lumen almost assumes its natural slit-like form leaving only extremely small areas, indicated at 14, where the catheter does not entirely comply with the wall of the lumen. Since the lumen wall tends to be irregular in cross-section throughout the length of the urethra there is overall an adequate seal to prevent urine from bypassing the catheter.

The portion of the catheter wall which affords compliance as described has an optimum thickness below 1 mm and preferably in the region of 0.25 mm and is produced from any flexural material which is clinically acceptable and yet sufficiently durable in use. Examples of material from which the tube may be formed are latex, silicone, urethane or polyvinylchloride.

The flexural properties of the tube will permit normal opening thereof when bladder pressure is applied to expel urine through the tube in the expanded urethra. Thus it will be seen that the collapsable-walled catheter having the aforesaid properties will permit substantially normal or any remaining sphincter muscle operation, and in this way simulation of a normal physiological function may be possible. This is in direct contrast to the constant drainage function of existing catheters.

Figure 2:
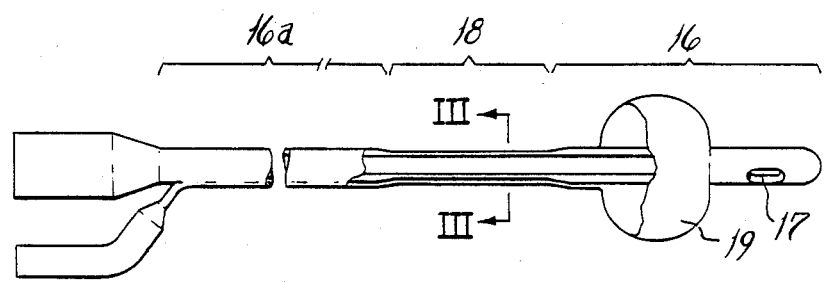
FIG. 2 illustrates a catheter made in accordance with the invention and including a Foley retention balloon which in use is situated within the bladder to prevent removal of the catheter.
Figure 3:
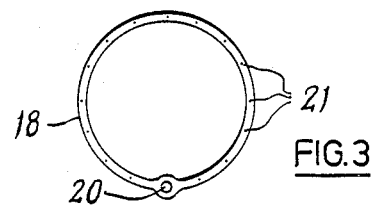
FIG. 3 is a section taken on line III—III of FIG. 2.

Referring now to FIG. 2, there is illustrated a catheter produced in accordance with the invention, wherein a first portion 16 consists of a semi-rigid tube of the conventional kind having an inlet 17. Extending distally from the portion 16 is a portion 18 of reduced wall thickness to the extent that its flexural properties are increased in accordance with the invention. The remaining portion 16a of the tube leading to the outlet distal end can, if required, be of conventional thickness and rigidity. It is the portion 18 which in use will be situated within the urethra, and its length is at least 3 cms, being a substantial proportion of the length of the adult female urethra. A Foley retention balloon 19 is formed on the portion 16 of the tube and is to be inflated by way of a small bore inflation tube 20 which is built into the catheter wall. FIG. 3 illustrates the thin-walled and flexural characteristics of the tube in the portion 18 in its normal non-deformed state, and shows the inflation tube 20. Also illustrated in FIG. 3 is a series of spaced reinforcing fibres 21 preferably of nylon which may be incorporated to increase the longitudinal tensile strength of the thin-walled portion 18. These fibres may extend longitudinally of the catheter throughout its length, and may be arranged helically to increase resistance to torsional forces in use.

Figure 4:
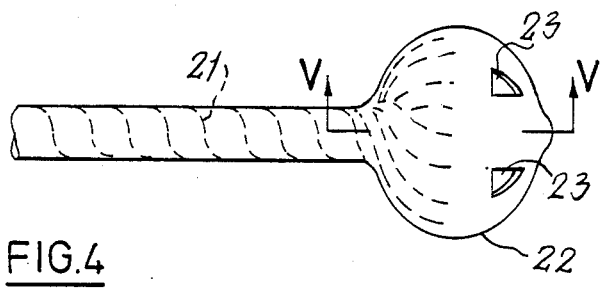
FIG. 4 illustrates a catheter made in accordance with the invention but including an integral, non-inflatable head of known type for insertion into the bladder.
Figure 5:
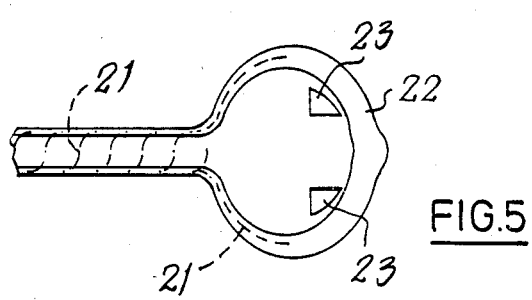
FIG. 5 is a section taken on line V—V of FIG. 4.

In FIG. 4 there is illustrated a catheter made in accordance with the invention having a series of helical reinforcing fibres 21. At the proximal end of this catheter there is a modified and enlarged malecot head 22, the reinforcing fibres 21 extending part way into the head. The head 22 includes a number of inlet apertures 23, and FIG. 5 illustrates how the wall thickness increases gradually into the head 22 from the tubular portion. Here again, the tube may consist of a portion of increased flexural properties, or alternatively the whole of the catheter tube may be in this form. It will be clear that the head 22 replaces the inflatable device 19 thus obviating the need for an inflation tube which could interfere with the compliance of the tube in use. This catheter is inserted into the bladder using a rod over which the catheter is placed, the rod being removed after insertion. The relatively thin walled part of the head 22 adjacent the tube permits the head to assume a degree of compliance with the neck of the bladder thus ensuring a good seal and preventing any tendency for urine to be forced into the space between the tube and the lumen, whilst the increased wall thickness towards the proximal end of the head provides improved stiffness for the head to maintain its shape in use.

Figure 6:
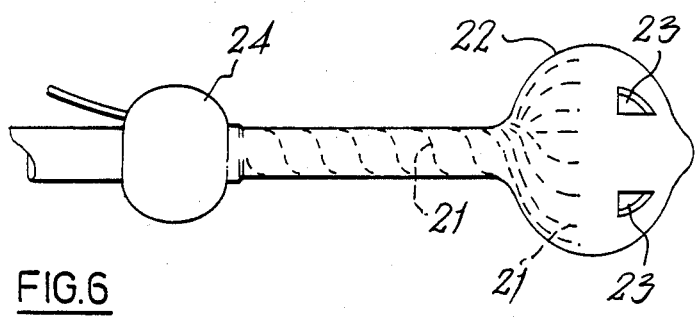
FIG. 6 illustrates a further embodiment as a modification of the catheter illustrated in FIG. 4.

In FIG. 6 there is illustrated a modified form of the catheter illustrated in FIG. 4. In this case, the portion of the tube which in use will be outside of the urethra, is of increased rigidity thus allowing a sliding balloon cuff 24 to be placed on the tube, effectively to anchor the catheter in the urethra and prevent pistoning of the head 22 within the bladder. Again this arrangement provides a more efficient seal.

Referring now to FIG. 7 the flexural portion of the tube in any of the embodiments described above may be preformed such that it assumes a flatter configuration in the absence of transmural pressure. This formation will allow the tube to collapse almost completely while still permitting compliance to the slit-like lumen. This cannot be achieved in a tube of circular cross-section since an increasing bending moment is generated as the radius of curvature decreases. A fully collapsible tube of the kind illustrated in FIG. 7 is known to act inherently as a valve requiring a certain minimum internal pressure before the flattened walls can be distended. Thus it will be seen that the tube can be formed to remain fully closed naturally under normal conditions until a bladder pressure equivalent to that applied when the bladder is, say, substantially filled, is attained, whereupon the tube will open to permit natural flow.

The normal maximum closure pressure which occurs naturally in the urethra to close the lumen is in the region of 60 centimeters water gauge in males and approximately 40 centimeters water gauge in females. Accordingly, the flexural wall portion of the catheters produced in accordance with this invention must ensure substantially complete collapse of the tube at the appropriate transmural pressure occurring in the urethra. For at least partial success it is considered that the tube must be collapsed to less than half its normal cross-sectional area at the appropriate closure pressure. Thus, whilst we have defined the tube as being sufficiently flexural that the maximum transmural pressure required to reduce the cross-sectional area of the tube from its normal state by 50% is 100 centimeters water gauge, this figure will be selected to match the natural average closure pressure of the patient, and indeed for preference, the tube should be even further collapsed at the appropriate pressure. Ideally, the internal cross-sectional area of the tube should be capable of reduction substantially to zero but be free to expand sufficiently to achieve the required rate of flow during micturition.

Since the flexural properties of the tube have been increased to the extent that bypassing is minimised by the ability of the tube to conform to the urethral wall over the normal range of pressures and during micturition, it may be possible to incorporate a non-return valve in the tube proximal to the flexural portion thereof which would pass urine automatically when a certain bladder pressure has been attained. Alternatively, or in addition, the tube itself may effect valving as described in relation of FIG. 7.

Certain clear advantages accrue from the use of the catheter produced in accordance with the invention. Initially, the catheter is a thin sleeve which lines the urethra and conforms to its slit-like shape thus to drain urine intermittently or continuously into a container. Further, the catheter has a low flexural resistance so that it can conform accurately to the slit-like shape of the lumen producing minimum discomfort and damage to the urethra. The catheter will have a high compliance to this shape in the normal range of urethral pressures and can collapse to ensure minimum urethral distension and irritation. Since it conforms to the urethral shape, bypassing of urine is reduced which in turn prevents irritation, encrustation, internal infection, and the passage of bacteria from external sources. The catheter is expected to ensure increased comfort and reassurance to the patient thus substantially reducing the natural anxiety and loss of dignity experienced under catheterisation.

We claim:

1. A urethral catheter comprising a resilient tube open at the proximal and distal ends respectively, the tube wall, throughout at least a portion of that part of the tube to be situated within the urethra, being deformable; having a certain normal cross-sectional area in an open, non-deformed state, to which it returns freely in the absence of external transmural pressure; being sufficiently compliant to conform freely to the internal shape of the urethral lumen thereby substantially preventing the by-pass of urine; and being sufficiently self supporting and flexural to an open configuration such that the maximum transmural pressure required to collapse the tube to half said normal cross-sectional area is 100 cm water gauge.

2. A urethral catheter according to claim 1, wherein said portion is sufficiently flexural that the transmural pressure required to collapse the tube to half of its normal cross-sectional area is less than 70 centimeters water gauge.

3. A urethral catheter according to claim 1, wherein the flexural characteristics of said tube portion are such that the tube is substantially fully collapsed and occluded at normal urethral pressures, i.e. in the region of 40 to 70 centimeters water gauge.

4. A urethral catheter according to claim 1, including a wall portion of increased rigidity with respect to said flexural portion at the proximal end of the latter, there being a Foley retention balloon around said portion of increased rigidity, and an inflation tube therefor passing longitudinally through the tube wall.

5. The urethral catheter according to claim 1, including a malecot head integral with the proximal end of the tube and having increasing wall thickness from its junction with the tube towards the proximal end of the catheter.

6. A urethral catheter according to claim 1, having one or more reinforcing fibres extending generally longitudinally of the tube wall.

7. A urethral catheter according to claim 6, wherein the or each said reinforcing fibre extends helically along said tube.

8. A urethral catheter according to claim 1, including a wall portion of increased rigidity at the distal end of said flexural wall portion and having thereon a sliding balloon cuff, the proximal end of said catheter including a retention head whereby the head and the cuff together serve to anchor the catheter in position.

9. A urethral catheter according to claim 1, in which at least a part of said tube is preformed to assume a normally flattened configuration such that the tube remains substantially closed until a minimum internal pressure is attained.

10. A urethral catheter according to claim 1, wherein the thickness of said flexural wall portion is less than 1 mm.

11. A urethral catheter according to claim 1, wherein said flexural portion is at least 3 cms in length.

* * * * *